United States Patent [19]

Holst et al.

[11] 4,117,222

[45] Sep. 26, 1978

[54] PROCESS FOR THE MANUFACTURE OF ABSORBENT, MODIFIED STARCH ETHERS AND THEIR USE

[75] Inventors: Arno Holst, Wiesbaden-Biebrich; Michael Kostrzewa, Wiesbaden; Gerhard Buchberger, Wiesbaden-Auringen, all of Fed. Rep. of Germany

[73] Assignee: Hoechst Aktiengesellschaft, Fed. Rep. of Germany

[21] Appl. No.: 819,944

[22] Filed: Jul. 28, 1977

[30] Foreign Application Priority Data

Jul. 31, 1976 [DE] Fed. Rep. of Germany ....... 2634539

[51] Int. Cl.$^2$ ............................................. C08B 31/08
[52] U.S. Cl. .................................... 536/50; 128/284; 128/290 P; 536/106; 536/111
[58] Field of Search .................. 536/50, 111, 106, 87; 128/290 P

[56] References Cited

U.S. PATENT DOCUMENTS

| 3,077,468 | 2/1963 | Geurden | 536/87 |
| 3,208,994 | 9/1965 | Flodin | 536/56 |
| 3,542,759 | 11/1970 | Gelotte et al. | 536/56 |
| 3,622,562 | 11/1971 | Muetgeert | 536/11 |
| 3,849,387 | 11/1974 | Fowells et al. | 526/88 |
| 3,936,441 | 2/1976 | Holst et al. | 536/87 |
| 3,965,091 | 6/1976 | Holst et al. | 536/87 |

FOREIGN PATENT DOCUMENTS

| 1,199,090 | 7/1970 | United Kingdom | 536/111 |
| 1,387,282 | 3/1973 | United Kingdom. | |

OTHER PUBLICATIONS

Chemical Abstracts, vol. 83, No. 12, Sep. 22, 1975, p. 99556j.

*Primary Examiner*—Ronald W. Griffin
*Attorney, Agent, or Firm*—James E. Bryan

[57] ABSTRACT

This invention relates to an improvement in the process for the manufacture of modified starch ethers in which, prior to, during, or after etherification, a reaction with a modifying agent is conducted in a wet alkaline medium, the improvement comprising that, if etherification were the only reaction conducted, an at least preponderantly water-soluble starch ether would be formed, and the modification results in an absorbent modified starch ether more than 40 per cent by weight of which is insoluble in water.

5 Claims, No Drawings

PROCESS FOR THE MANUFACTURE OF ABSORBENT, MODIFIED STARCH ETHERS AND THEIR USE

The present invention relates to a process for the manufacture of absorbent, modified starch ethers and to the use of the compounds according to the invention.

Absorbent, high molecular weight compounds are of great importance, e.g., as an addition to or the only component of masses capable of absorbing physiological body fluids, such as urine, blood, perspiration or saliva in the fields of infant care, feminine hygiene, in medical practices and in hospitals. The use of the most varied polysaccharides or their derivatives has been repeatedly described (see, e.g., German Pat. Nos. 559,555 and 592,455). At the present time, the absorbent bodies in tampons, sanitary towels, and diapers still consist preponderantly of cellulose. Another field of application in which absorbent high molecular weight compounds may be of use is the dehydration of aqueous emulsions.

Starch ethers have been known for a long time. Methods for the preparation thereof are described, e.g., in R. L. Whistler's "Methods in Carbohydrate Chemistry", Academic Press, New York and London, Vol. IV, pages 304 to 312 (1964).

The properties of starch or starch ethers may be modified by chemical reactions, e.g. cross-linking. U.S. Pat. No. 3,077,468, discloses a process for reducing the water-solubility of hydroxy alkyl ethers of starch, in which unsaturated bi-functional aliphatic acids and the anhydrides thereof are used as cross-linking agents. The resulting products may be used for the manufacture of films or protective coatings.

A starch derivative which may be used for making canned preserves and is disclosed in German Offenlegungsschrift No. 2,204,468, is a hydroxypropyl ether of starch which was cross-linked with epichlorohydrin. A starch ether modified in this manner is particularly suitable as a thickener for cake fillings, puddings, soups or sauces, because it has controlled viscosity and thermal conductivity properties. ideal, German Auslegeschrift No. 1,570,191, discloses a process for the preparation of substitution products of copolymers which are distinguished by special swelling characteristics. According to the process, a copolymer, e.g. a copolymer of starch and an aliphatic bi-functional compound in which the functional groups are a halogen or an epoxy group, is reacted with an etherifying agent which is an epoxide or a compound capable of forming epoxides in an alkaline medium. Compounds of this type are insoluble, but swellable in water and permit the application of molecular sieves.

British Pat. No. 1,199,090, discloses a process for the etherification of starch in which the starch is reacted in an aqueous suspension and under alkaline conditions first with a cross-linking agent and then with an etherifying agent in such a manner that swelling of the starch derivative is avoided.

The cross-linked starch ethers known from the prior art are incapable of absorbing relatively large quantities of water and, as far as possible, retaining it without being themselves substantially dissolved.

It is the object of the present invention to provide a process for the manufacture of absorbent, modified starch ethers and to provide applications of the starch derivatives produced according to the process of the invention.

The present invention is based on a process for the manufacture of modified starch ethers in which, prior to, during or after etherification, a reaction with a modifying agent is conducted in a wet alkaline medium. In the process of the invention, if etherification were the only reaction performed, an at least preponderantly water-soluble starch ether would be formed, and the modification results in an absorbent modified starch ether more than 40 percent by weight of which is insoluble in water.

For the manufacture of the inventive products, the alkalizing agent used for starch, e.g. potato starch or corn starch, is almost invariably an aqueous NaOH solution, for reasons of economy, but other aqueous alkalies, such as KOH or LiOH solutions, also may be used as alkalizing agents.

Monochloroacetic acid, sodium monochloroacetic acid, methyl chloride, ethylene oxide or propylene oxide, either alone, or in the form of mixtures of two or more thereof, are primarily used as etherification agents for the preparation of the starch ethers according to the invention, but ethyl chloride, especially in admixture with ethylene oxide or propylene oxide, also may be used. The ethers prepared from alkalized starch and these reagents, e.g. carboxy methyl starch (CMS), methyl starch (MS), hydroxy ethyl starch (HES), hydroxy propyl starch (HPS), methyl hydroxy ethyl starch (MHES), and other starch ethers or mixtures of starch ethers should have a degree of substitution (D.S.) or M.S. (molecular substitution) such that they are predominantly water-soluble, i.e. to more than 80 percent by weight, frequently to more than 95%.

In addition to a known etherification reaction, a modification reaction is conducted in the process according to the invention. The modifying process is performed in such a manner that the resulting modified starch ethers are more than 40 percent by weight water-insoluble, but capable of absorption; i.e. they can absorb relatively large quantities of water and more or less retain it without being completely dissolved.

Preferably, the modification reaction is a cross-linking reaction. For this purpose, the cross-linking agents defined below may be used, in quantities preferably ranging from 0.0005 to 0.2 part by weight per part by weight of starch, depending on which agent is used. In these cross-linking agents, the functional groups capable of a reaction with the hydroxyl groups of the starch or of the starch ethers may be one of the following groups:

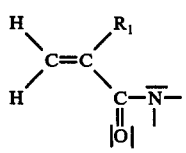 the acrylamido group wherein $R_1 = H$ or $CH_3$ or

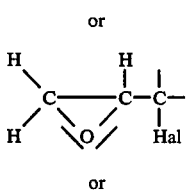 an α-halogen epoxy group wherein Hal = Cl or Br or

-continued

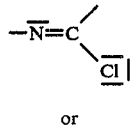
the chloro azomethine group or

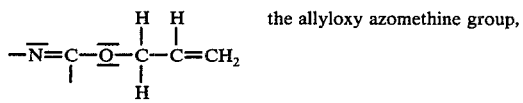
the allyloxy azomethine group, or the known cross-linking agent phosphorus oxychloride may be used.

Dichloroacetic acid also may be used as a cross-linking agent, but in this case at least 0.01 part by weight of cross-linking agent must be used per part by weight of starch. Also, if monochloroacetic acid is used as the etherification agent, either alone or in admixture with ethylene oxide, the quantity of the cross-linking agent, in the case of dichloroacetic acid, must be relatively large as compared with the quantity of monochloroacetic acid.

The following are exemplary of compounds containing the above-mentioned functional groups:
Methylene-bis-acrylamide,
bisacrylamido-acetic acid,
N,N'-dimethylol methylene bisacrylamide,
1,1-bis-acrylamido-ethane,
methylene-bis-methacryl-amide,
epichlorohydrin,
2,4,6-trichloro-pyrimidine,
2,4,5,6-tetrachloro-pyridimine,
cyanuric chloride, and
triallyl cyanurate.

Alternatively, a modification reaction may be performed in which, instead of a reaction between the starch ether molecules, another chemical reaction at these molecules occurs. For this purpose, one of the following modifying agents may be used, of which preferably 0.01 to 0.3 part by weight per part by weight of starch is required, depending upon the type of modifying agent used.

These modifying agents are capable of a mono-functional reaction with the hydroxyl groups of starch or starch ethers in an alkaline medium and are illustrated by one of the following formulae:

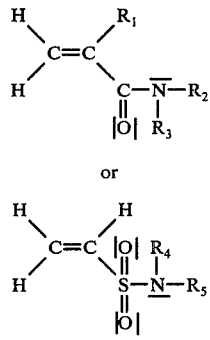

wherein
$R_1$ = $CH_3$ or H,
$R_2$ = H, and
$R_3$ = $CH_3$, $CH_2OH$, an N-methylene-acylamido group with 1 to 3 carbon atoms, an esterified N-methylene-carbamido group or N-carboxy methylene carbamido group with 2 to 7 carbon atoms, or
$R_2$ and $R_3$ are identical and are $CH_3$ or $CH_2OH$,
and wherein
$R_4$ and $R_5$ = H, or $R_4$ = H and $R_5$ = $CH_3$, or
$R_4$ and $R_5$ are identical and are $CH_3$.

The following substances are exemplary of compounds covered by these general formulae:
N-methylol-acrylamide,
N-methyl-acrylamide,
N-methylol-methacrylamide,
N-methyl-methacrylamide,
N-(acrylamido-methylene)-formamide,
N-(acrylamido-methylene)-acetamide,
N-(acrylamido-methylene)-methylurethane,
N-(acrylamido-methylene)-amylurethane,
N-(acrylamido-methylene)-methoxy-ethyl-urethane
N-(acrylamido-carboxy-methylene)-ethyl-urethane,
Vinyl-sulfonamide,
N-methyl-vinyl-sulfonamide, and
N,N'-dimethyl-vinyl-sulfonamide.

For the preparation of the starch ethers modified by cross-linking or some other reaction, an alcohol with 1 to 6 carbon atoms, such as methanol, ethanol, isopropanol, n-butanol, tert.-butanol or cyclohexanol, is preferably used as the liquid reaction medium, the more so as these organic solvents, especially the higher alcohols, react only slightly or not at all with the reactants. Preferably, isopropanol is used as the alcohol, advantageously in the form of the technical product which contains about 13 percent by weight of water. During the various steps of the process, more water, in addition to that introduced by the use of aqueous isopropanol, is added to the reaction mixture by the water contained in the alkali hydroxide solution. In some cases, additional quantities of water are added to the reaction mixture, because the cross-linking agent or other modifying agent is added in the form of an aqueous solution.

However, the total quantity (by weight) of water introduced into the reaction mixture should not exceed the quantity (by weight) of isopropanol contained therein. The organic solvent used as the liquid reaction medium, preferably in a quantity ranging from 0.2 to 5 parts by weight per part by weight of starch, is frequently present at all stages of the process (alkalization, modification, and etherification), but also may be present in one or the other of the process steps only.

If one of the above-mentioned liquid organic reaction media is used, there are four possibilities of performing a modification by cross-linking or some other chemical reaction, to which the following parameters apply:
  Modification is carried out during alkalization over a period of from about 15 to 45 minutes and at a temperature of about 25° C.
  Modification is carried out after alkalization, but prior to etherification, over a period of from about 30 to 60 minutes and at a temperature of about 25° to 85° C.
  Modification is carried out during (i.e. simultaneously with) etherification over a period of from about 45 to 75 minutes and at a temperature of about 30° to 85° C.
  Modification is carried out after etherification, over a period of from about 30 to 60 minutes and at a temperature of about 50° to 75° C.

If water is used as the reaction medium, in accordance with another embodiment of this invention, highly absorbent modified starch ethers are likewise obtained. For this embodiment of the inventive process, the starch is advantageously modified during or after alkalization, because in this manner, gelatinization of the starch may be at least substantially avoided. In this case, the moisture component of the reaction medium includes only the water contained in the starting materials, e.g. in the crude starch, the aqueous alkali hydroxide solution, or in the modifier. There are two ways of performing this method, with the following parameters:

Modification is carried out during alkalization over a period of from about 15 to 45 minutes at a temperature of about 25° C.

Modification is carried out after alkalization, but prior to etherification, over a period of from about 30 to 60 minutes and at a temperature of about 25° to 85° C. on or If the process of the invention is performed as outlined above, products are obtained which still contain a certain water-insoluble portion. For many applications, such a portion does not matter, so that a removal of the water-soluble component is not normally necessary. For some finishing processes to which the absorbent starch ethers obtained by the above described process are subjected, this water-soluble component is even of advantage, because it improves the adhesion of the product on or to a support.

The absorbent starch ethers produced according to the process claimed in the present application are obtained in the form of a powder or more often in granulate form, the powder being easily converted into a granular form by known processes, if desired. The granulated absorbent starch ethers lend themselves particularly readily to further processing. They are ball-shaped and thus favor the transmission of liquids. After a certain time interval, the granulates decompose into smaller particles which are, in turn, capable of unlimited further swelling. It is assumed that the almost ideal, ball-shaped swelling and the hollow spaces formed within the modified starch ether structure are responsible for the easy transmission of liquids.

The above-described absorbent starch ethers are particularly suitable for the absorption of physiological body fluids, such as urine, blood, perspiration or saliva, in the form of infant care, feminine hygiene, in medical practices, or in hospitals, but they also may be used, for example, for dehydrating aqueous emulsions. For applications in which they cannot simply be used in the form in which they are obtained when the present process is performed, the starch ethers according to the invention may be further treated according to one of the following methods.

The particulate, absorbent, modified starch ether is attached to at least one surface of a strip of hydrophilic material which serves as the support, and is then dried. For this method, the starch ethers may be used in any particular form, especially in the form of flowable, suspendable, or electrostatically flockable particles. For some embodiments of the inventive process, the maximum size of the particles is not important and may be 1 mm or more. In normal practice, however, the particle size ranges from about 0.05 to 0.04 mm. A water-soluble portion of at least 15 percent by weight is of advantage in most cases, because it improves the adhesion of the modified starch ether particles to the hydrophilic strip; the water-soluble portion should not exceed about 60 percent by weight, however. The hydrophilic strip used as the support advantageously is composed of a woven or knitted fabric, a fleece, or preferably paper composed of cellulose, mechanical wood pulp, or synthetic fibers, especially polyolefin fibers, such as those described in German Offenlegungsschrift No. 2,117,370, or a mixture of such substances, and it possesses a certain absorbing and retaining capacity for liquids. As a rule, the weight per unit area of this material is between 12 and 500 g/m². Several methods may be employed for carrying out such a process.

According to one such method, at least one of the surfaces of the strip of hydrophilic material is wetted with water and the wetted surface is then covered with the particulate modified starch ether. In the simplest case, wetting of the support surface is carried out by a brief immersion of the strip in water and squeezing out until the desired degree of humidity is reached. Application of the swellable particles may be effected, e.g., by scattering the starch ether powder onto the wet surface of the strip, or by whirler-coating in a turbulence chamber. In another method, which also may be employed, the surface of the support is covered by dispersing the modified starch ether in a solution containing an unmodified starch ether or cellulose ether in an organic solvent, to which water may be added, and coating the support with the resulting dispersion. Suitable unmodified starch ethers or cellulose ethers are particlarly those water-soluble ethers which have a viscosity within the range from about 10 to 30,000 cP in a 2 percent aqueous solution at 20° C.

An alcohol with 1 to 4 carbon atoms, a ketone, such as methyl ethyl ketone or diethyl ketone, a chloroderivative of methane, such as methylene chloride or chloroform, or, most advantageously, mixtures of such solvents may be used as organic solvents. A roll coater may be used for coating the support with the dispersion.

In another of the possible methods, the modified starch ether is attached to the support by an electrostatic flocking process. For this purpose, at least one of the surfaces of the support is wetted with water, for example, by immersion, spraying, or impregnation, and the still wet material is then conducted through a high-voltage electric field of up to 100 kV. One of the two electrodes causing the electric field is constructed as a sieve or a perforated plate and serves to accommodate the modified starch ether. The counter-electrode is designed as a flat surface and may serve, in addition to its electrostatic use, also as a support for the material to be flocked.

Similar processes have been proposed in other fields, e.g. for the processing of modified cellulose ethers.

The resulting strip-shaped materials composed of a support and an absorbent modified starch ether are highly absorbent and are further distinguished by good liquid retention properties. Because they lend themselves easily to further treatments, they may be incorporated with particular advantage — as underlayers, intermediate layers, or top layers — in laminated sheets, as are required, for example, in the field of hygiene, for use as sanitary towels, diapers, or bed undersheets, in order to positively influence the absorption behavior of these materials.

Other ways of applying the absorbent modified ethers also may be considered, such as those described in German Offenlegunsschrift No. 2,364,628, for hydrophilized shaped bodies composed of a water-insoluble polymer capable of forming fibers and films, especially cellulose hydrate, cellulose acetate, a cellulose ether, or a polyalkylene. This known structure comprises absorbent modified cellulose ether particles which are evenly distributed in the polymer mass or are applied to at least one surface of the film, if the polymer is in the form of a film.

In the following examples, all percentages are by weight. Alkalization, etherification, and modification are carried out at the temperatures stated and while intensively mixing the reactants. The values obtained from the test products are as follows:

WRC = water retention capacity in percent by weight, measured at 2000 times the acceleration of gravity and based on the water-insoluble portion of the total product, WIP = water-insoluble portion in percent by weight of the total product, $AC_{NaCl}$ = absorption capacity for 1 percent NaCl solution in percent by weight, calculated on the total product.

The WRC value is determined after immersion of the sample in water. The $AC_{NaCl}$ value is determined after the sample has absorbed 1 percent NaCl solution to the point of saturation.

The values determined in the examples for the water retention capacity range from about 500 to 10,000 percent, the values for the water-insoluble component of the starch ethers range from about 40 to 95%, and the values for the NaCl absorption capacity range from about 900 to 1,800 percent.

In Examples 1 to 17, the compounds are modified by cross-linking, and in Examples 18 to 28 they are modified by another chemical reaction.

Examples 29 and 30 were taken from prior publications and serve to compare prior art compounds with the modified starch ethers produced by the process according to the present invention.

EXAMPLE 1

100 g of potato starch (14% by weight water content) are mixed with 92 g of a 50 percent by weight aqueous NaOH solution and 1 g of bisacrylamido-acetic acid, as a cross-linking agent, and kneaded for 30 minutes at about 25° C. 93 g of sodium monochloro acetate are added to the mixture in several batches and the mass is etherified for 1 hour at a temperature of about 60° C. The reaction mixture is then neutralized with glacial acetic acid against phenolphthalein, filtered, and the residue is washed several times with 80 percent by weight aqueous methanol until it is free of salt and then dried at about 60° C. WRC = 3,060; WIP = 70.6; $AC_{NaCl}$ = 1.570.

EXAMPLE 2

100 g of potato starch (14% by weight water content) are mixed with 160 g of a 50 percent by weight aqueous NaOH solution and alkalized for 30 minutes at about 25° C. 1.54 g of methylene-bisacrylamide, as a cross-linking agent, are added in portions to the mixture and the mixture is reacted for 30 minutes at a temperature of about 50° C. Then, 94.5 g of an 80 percent by weight aqueous monochloroacetic acid solution are added and the mass is etherified for one hour at a temperature of about 60° C. Further processing is as in Example 1. WRC = 2,120; WIP = 86.8; $AC_{NaCl}$ = 1,200.

EXAMPLE 3

The procedure described in Example 1 is repeated, except that 1.16 g of epichlorohydrin are added as the cross-linking agent. WRC = 1.574; WIP = 71.5; $AC_{NaCl}$ = 1,450.

EXAMPLE 4

200 g of potato starch (14% by weight water content) are mixed with 66 g of isopropanol (87% by weight) and 24 g of a 50 percent by weight aqueous NaOH solution, and kneaded for 15 minutes at about 25° C. 1 g of bisacryl amido acetic acid, as a cross-linking agent, is added to the mixture in portions and the mixture is then reacted for 15 minutes at about 25° C. Then, an additional 160 g of a 50 percent by weight aqueous NaOH solution are dropwise added and the mixture is alkalized for 30 minutes at about 25° C. Finally, 186 g of sodium monochloro acetate are added in several portions and the mass is etherified for 1 hour at about 60° C. Further processing is as described in Example 1. WRC = 2,840; WIP = 86.1.

EXAMPLE 5

The procedure described in Example 4 is repeated, except that 5 ml of phosphorus oxychloride are added as the cross-linking agent. WRC = 1,736; WIP = 67.0.

EXAMPLE 6

200 g of potato starch (14% by weight water content) are mixed with 725 ml of isopropanol (87% by weight) and 24 g of a 50 percent by weight aqueous NaOH solution, and the mass is kneaded for 30 minutes at about 25° C. 14.8 g of an 80 percent by weight aqueous monochloroacetic acid solution and 0.5 g of bis-acrylamido acetic acid, as a cross-linking agent, are added to the mixture, and the mass is cross-linked and etherified for 1 hour at about 60° C. Further processing is as described in Example 1. WRC = 1,878; WIP = 94.2.

EXAMPLE 7

400 g of potato starch (14% by weight water content) are mixed for 45 minutes and at about 25° C with 854 g of isopropanol (87% by weight) and 80 g of a 50 percent NaOH solution. 100 g of a 30 percent aqueous solution of N,N'-dimethylol-methylene-bis-acrylamide, as a cross-linking agent, are drop-wise added and the mixture is reacted for 1 hour at about 50° C. Then 93 g of sodium monochloroacetate are added in several portions and the mixture is etherified for one hour at about 70° C. Further processing is as described in Example 1. WRC = 2,680; WIP = 92.3.

EXAMPLE 8

344 g of potato starch, which had been dried at about 60° C, are mixed for 30 minutes at about 25° C with 1,000 g of isopropanol (87% by weight) and 48 g of a 50 percent by weight aqueous NaOH solution. 29.1 g of sodium monochloroacetate are added to the mixture in several portions and the mass is etherified for 1 hour at about 60° C. Then 12.9 g of dichloro acetic acid are added, in portions, as a cross-linking agent, and the mass is reacted for one hour at about 60° C. Further processing is as in Example 1. WRC = 2,120; WIP = 86.8.

EXAMPLE 9

The procedure described in Example 6 is repeated, except that 66 g of isopropanol (87% by weight), 80 g of a 50 percent aqueous NaOH solution, and 93.2 g of sodium monochloroacetate are used. Cross-linking is effected by adding 11.5 g of trichloro pyrimidine and proceeds for 1 hour at about 80° C. WRC = 4,230; WIP = 67.5.

EXAMPLE 10

The procedure described in Example 7 is repeated, except that 100 g of potato starch (14% by weight water content), 300 g of isopropanol (87% by weight) and 160 g of a 50 percent by weight aqueous NaOH solution are used and the mass is mixed for 30 minutes. Cross-linking proceeds for 1 hour at 80° C after the addition of 10.9 g of tetrachloro-pyrimidine, and etherification proceeds within 1 hour at about 80° C after the addition of 94.5 g of an 80 percent by weight aqueous monochloroacetic acid solution. WRC = 3,740; WIP = 72.3.

EXAMPLE 11

The procedure described in Example 10 is repeated, except that the cross-linking reaction proceeds for one hour at about 70° C after the addition of 10 g of a 5 percent solution of triallyl cyanurate in isopropanol. WRC = 560; WIP = 83.4.

EXAMPLE 12

The procedure described in Example 8 is repeated, except that 200 g of potato starch (14% by weight water content), 600 g of isopropanol (87% by weight) and 60 g of a 50 percent by weight aqueous NaOH solution are used. Etherification proceeds with 69.9 g of sodium monochloroacetate at about 70° C, and cross-linking occurs after the addition of 1.85 g of cyanuric chloride at about 70° C. WRC = 1,270; WIP = 61.4.

EXAMPLE 13

The procedure described in Example 1 is repeated, except that 0.42 g of 1,1-bis-acrylamido ethane is used as the cross-linking agent. WRC = 3,745; WIP = 68.4; $AC_{NaCl}$ = 1,630.

EXAMPLE 14

The procedure described in Example 6 is repeated, except that a solution of 722 ml of isopropanol (87% by weight) and 20 g of sodium hydroxide is used. Cross-linking and etherification proceed simultaneously for 1 hour at about 30° C and then for another hour at about 70° C, after adding 0.14 g of methylene-bis-acrylamide and 88 g of ethylene oxide. WRC = 9,500; WIP = 62.3.

EXAMPLE 15

The procedure described in Example 14 is repeated, using, however, 6.5 g of dichloroacetic acid as the cross-linking agent. WRC = 1,053; WIP = 82.1.

EXAMPLE 16

The procedure described in Example 2 is repeated, except that 224 g of a 50 percent by weight aqueous NaOH solution is used. Cross-linking proceeds for one hour with 15.4 g of methylene bisacrylamide, and etherification is effected in a pressure vessel for 1 hour at about 85° C with 50 ml of ethylene oxide and 800 ml of methyl chloride. WRC = 1,913; WIP = 61.4; $AC_{NaCl}$ = 1,100.

EXAMPLE 17

The procedure described in Example 16 is repeated, except that methyl chloride is used as the only etherification agent. WRC = 1,785; WIP = 62.0.

EXAMPLE 18

400 g of potato starch (14% by weight water content) are mixed for 45 minutes and at a temperature of approximately 25° C with 854 g of isopropanol (87% by weight) and 368 g of a 50 percent by weight aqueous NaOH solution. Then 245 g of sodium monochloroacetate are added and the mixture is etherified for 1 hour at about 70° C. 47 g of a 60 percent by weight aqueous solution of N-methylol-acrylamide, as a modifier, are drop-wise added and the mixture is reacted for one hour at about 50° C. Further processing is as in Example 1. WRC = 2,698; WIP = 55.8.

EXAMPLE 19

150 g of potato starch (14% by weight water content) are mixed for 30 minutes, at a temperature of approximately 25° C, with 63.2 g of a 50 percent by weight aqueous NaOH solution. Then 4.23 g of vinyl sulfonamide are added as a modifier and the mixture is reacted for 30 minutes at about 50° C. Then 73.6 g of sodium monochloroacetate are added and the mass is etherified for 1 hour at about 70° C. Further processing is as in Example 1. WRC = 3,873; WIP = 52.4.

EXAMPLE 20

150 g of potato starch (14% by weight water content) are mixed for 30 minutes at a temperature of approximately 25° C with 50 g of isopropanol (87% by weight) and 63.2 g of a 50 percent by weight aqueous NaOH solution. 15 g of acrylamido methylene acetamide are added to the mixture as a modifier and the mixture is reacted for 1 hour at about 50° C. Then 73.6 g of sodium monochloroacetate are added and the mass is etherified for 1 hour at about 70° C. Further processing is as in Example 1. WRC = 1,371; WIP = 76.9; $AC_{NaCl}$ = 950.

EXAMPLE 21

The procedure described in Example 20 is repeated, except that the potato starch is mixed for 45 minutes with 126.4 g of a 50 percent by weight aqueous NaOH solution and 450 g of isopropanol (87% by weight). 5 g of acrylamido methylene formamide are used for modification and 147.2 g of sodium monochloroacetate for etherification. WRC = 7,189; WIP = 45.7.

EXAMPLE 22

150 g of potato starch (14% by weight water content) are mixed with 63.2 g of a 50 percent by weight NaOH solution and reacted for 30 minutes at about 25° C with 16.9 g of acrylamido methylene amyl urethane as a modifier. Then the mixture is etherified for one hour at about 70° C with 73.6 g of sodium monochloroacetate. Further processing is as in Example 1. WRC = 2,142; WIP = 71.4; $AC_{NaCl}$ = 1,070.

EXAMPLE 23

The procedure described in Example 20 is repeated, except that 6.24 g of acrylamido methylene methyl urethane are used as the modifier. WRC = 2,763; WIP = 62.7.

EXAMPLE 24

The procedure described in Example 21 is repeated, except that 19.4 g of acryl amido carboxy methylene ethyl urethane are used as the modifier. WRC = 1,795; WIP = 72.5.

EXAMPLE 25

The procedure described in Example 19 is repeated, except that the potato starch is mixed for 45 minutes at about 25° C with 126.4 g of the 50 percent by weight aqueous NaOH solution. 7.98 g of acrylamido methylene methoxy ethyl urethane are added as the modifier and the mixture is reacted for one hour at about 50° C. Then, 147.2 g of sodium monochloroacetate are added for etherification. WRC = 4,378; WIP =75.7; $AC_{NaCl}$ = 1,760.

EXAMPLE 26

100 g of potato starch (14% by weight water content) are mixed for 30 minutes at a temperature of about 25° C with 300 g of isopropanol (87% by weight) and 40 g of a 50 percent by weight aqueous NaOH solution. 5 g of acrylamido methylene acetamide are added and after about 5 minutes the mixture is conveyed into a pressure vessel. 112 ml of ethylene oxide are added and the mixture is then etherified, first for 1 hour at about 30° C and then for another hour at about 70° C. Further processing is as in Example 1. WRC = 2,530; WIP = 64.1.

EXAMPLE 27

The procedure described in Example 26 is repeated, except that 5 g of acrylamido methylene formamide are added as the modifier. WRC = 2,210; WIP = 62.7; $AC_{NaCl}$ = 1,130.

EXAMPLE 28

The procedure described in Example 26 is repeated, except that 7.5 g of acrylamido methylene methyl urethane are used as the modifier. WRC = 1,644; WIP = 80.0.

EXAMPLE 29

It is impossible to produce a cross-linked starch by the method described in Example 12 of German Offenlegungsschrift No. 1,443,359 (which discloses a preliminary stage of the products according to German Auslegeschrift No. 1,570,191), because neither a solution nor a dispersion can be produced from starch, an aqueous NaOH solution, and a water-immiscible organic solvent. The resulting reaction mixture has a rubber-like consistency. For the reasons outlined, the planned further etherification according to German Auslegeschrift No. 1,570,191, cannot be accomplished.

EXAMPLE 30

A cross-linked starch ether is prepared in accordance with Example 1 of British Pat. No. 1,999,090:

A mixture of a 30 percent aqueous NaOH solution and a 26 percent aqueous NaCl solution is added to a 41 percent aqueous suspension of unmodified corn starch in such a manner that the resulting suspension contains 1.5 percent by weight of NaOH, based on the starch solids, and 4 percent by weight of NaCl, based on the water content. 1 percent by weight of epichlorohydrin is added (instead of 2% of divinyl sulfone; see table in Example 12 of the British patent), based on the starch component, and the mass is cross-linked for 4 hours at 38° C while stirring. The suspension is then diluted to a starch content of 20 percent by weight by adding water. Ethylene oxide is added and etherification is conducted at 38° C in a pressure vessel, until an M.S. of 0.5 has been attained (after about 4 hours).

The cross-linked hydroxyethyl starch thus obtained has a WRC of 95, a WIP of 96, and an $AC_{NaCl}$ of 50. If etherification with ethylene oxide is the only reaction, i.e. no cross-linking takes place, a water-insoluble starch ether results. Compared with the modified starch ethers produced by the inventive process of this application, it can not be termed "absorptive", and if etherification were the only reaction, no predominantly water-soluble starch ether would result.

It will be obvious to those skilled in the art that many modifications may be made within the scope of the present invention without departing from the spirit thereof, and the invention includes all such modifications.

What is claimed is:

1. In the process for the manufacture of a modified starch ethers in which, prior to, during, or after etherification, a reaction with a modifying agent is conducted in a wet alkaline medium.

the improvement comprising that in the etherification step an etherification agent selected from the group consisting of monochloroacetic acid, sodium monochloroacetic acid, methyl chloride, ethylene oxide, propylene oxide and ethyl chloride, alone or in the form of admixtures of two or more thereof is used, the ethers prepared from alkalized starch and said agents have a degree of substitution, without the modification step, such that they are more than 80 percent by weight water-soluble, the modifying step is performed with a modifying agent selected from the group consisting of (a) 0.0005 to 0.2 part by weight per part by weight of starch of (1) a cross-linking agent carrying one of the following functional groups capable of a reaction with hydroxyl groups:

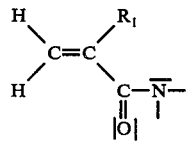

the acrylamido group wherein $R_1$ = H or $CH_3$, or

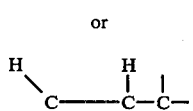

the α-halogen-epoxy group wherein Hal = Cl or Br, or

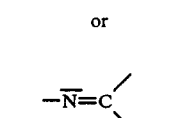

the chloro-azomethine group, or

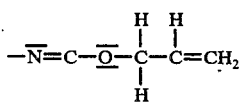

the allyloxy-azomethine group, or (2) phosphorus oxychloride, and (b) 0.01 to 0.3 part by weight per part by weight of starch of a compound capable of reacting monofunctionally with the hydroxyl groups of starch or of starch ethers under the reaction conditions, the compound having one of the following general formulae:

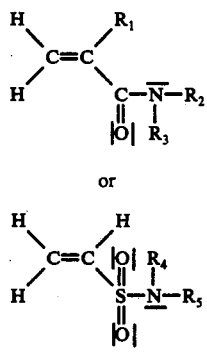

wherein
R₁ = CH₃ or H,
R₂ = H, and
R₃ = CH₃, CH₂OH, an N-methylene-acylamido group with 1 to 3 atoms, an esterified N-methylene-carbamido group or N-carboxy methylene carbamido group with 2 to 7 carbon atoms, or
R₂ and R₃ are identical and are CH₃, or CH₂OH, and wherein
R₄ and R₅ = H, or R₄ = H and R₅ = CH₃, or
R₄ and R₅ are CH₃, whereby the modification results in an absorbent modified starch ether more than 40 percent by weight of which is insoluble in water and the water retention capacity range of which is from about 500 to 10,000 percent.

2. A process for the manufacture of modified starch ethers according to claim 1 in which etherification and modification are conducted in the presence of an alcohol with 1 to 6 carbon atoms in such a manner that about 0.2 to 5 parts by weight of alcohol are used per part by weight of starch.

3. A process for the manufacture of modified starch ethers according to claim 2 in which the isopropanol is the alcohol.

4. A process for the manufacture of modified starch ethers according to claim 1 in which the modification reaction is performed during or after alkalization, but prior to etherification, in such a manner that the water contained in the starting materials is the only moisture present.

5. A process for converting the modified starch ethers produced according to the process claimed in claim 1 into a material which lends itself readily to further processing, which comprises attaching the particulate, absorbent starch ether to a strip of hydrophilic material serving as a support and the strip is then dried.